US012705741B2

(12) United States Patent
Kobold et al.

(10) Patent No.: US 12,705,741 B2
(45) Date of Patent: Aug. 11, 2026

(54) AUTOMATIC METHOD FOR SEGMENTATION OF A THROMBUS AND A LESION IN A THREE-DIMENSIONAL BRAIN IMAGE

(71) Applicants: UNIVERSITE D'EVRY VAL D'ESSONNE, Evry-Courcouronnes (FR); CENTRE HOSPITALIER SUD FRANCILIEN, Corbeil-Essonnes (FR)

(72) Inventors: Jonathan Kobold, Weilheim (DE); Vincent Vigneron, Evry Courcouronnes (FR); Hichem Maaref, Evry Courcouronnes (FR); Cosmin Alecu, Corbeil-Essonnes (FR); Didier Smadja, Corbeil-Essonnes (FR); Nicola Chausson, Corbeil-Essonnes (FR); Yann Lhermitte, Corbeil-Essonnes (FR)

(73) Assignees: UNIVERSITE D'EVRY VAL D'ESSONNE, Evry-Courcouronnes (FR); CENTRE HOSPITALIER SUD FRANCILIEN, Corbeil-Essonnes (FR)

( * ) Notice: Subject to any disclaimer, the term of this patent is extended or adjusted under 35 U.S.C. 154(b) by 302 days.

(21) Appl. No.: 18/576,644

(22) PCT Filed: Jul. 1, 2022

(86) PCT No.: PCT/EP2022/068270
§ 371 (c)(1),
(2) Date: Jan. 4, 2024

(87) PCT Pub. No.: WO2023/280708
PCT Pub. Date: Jan. 12, 2023

(65) Prior Publication Data

US 2024/0312008 A1 Sep. 19, 2024

(30) Foreign Application Priority Data

Jul. 6, 2021 (FR) ....................................... 2107286

(51) Int. Cl.
*G06T 7/00* (2017.01)
*G06T 5/40* (2006.01)
(Continued)

(52) U.S. Cl.
CPC .............. *G06T 7/0012* (2013.01); *G06T 5/40* (2013.01); *G06T 7/12* (2017.01); *G06T 15/00* (2013.01);
(Continued)

(58) Field of Classification Search
None
See application file for complete search history.

(56) References Cited

U.S. PATENT DOCUMENTS

| | | | | |
|---|---|---|---|---|
| 2020/0005464 A1* | 1/2020 | Weese | G06F 17/16 | |
| 2023/0255581 A1* | 8/2023 | Jang | A61B 6/032 | 382/128 |

(Continued)

OTHER PUBLICATIONS

Jonathan Kobold. Deep Learning for lesion and thrombus segmentation from cerebral MRI. Image Processing [eess.IV]. Université Paris Saclay (COmUE), 2019. English. NNT : 2019SACLE044. tel-03592570 Available online: https://theses.hal.science/tel-03592570v1 (Year: 2019).*

(Continued)

*Primary Examiner* — Tahmina N Ansari
(74) *Attorney, Agent, or Firm* — CUSHMAN PARTNERS, LLC

(57) ABSTRACT

A method for segmenting a thrombus and a lesion caused by the thrombus in a three-dimensional brain image, includes supervised training of a primary recurrent artificial neural network to provide a lesion prediction from an image;
(Continued)

supervised training of a secondary recurrent artificial neural network to provide a thrombus prediction from an image; using each trained primary recurrent artificial neural network on each image of a set of images obtained from the three-dimensional image, and merging the lesion predictions obtained to obtain a set of lesion segmentations: if the set of lesion segmentations includes a segmentation, selecting the widest segmentation as the lesion segmentation; using each trained secondary recurrent artificial neural network on each image of a set of secondary images obtained from the three-dimensional image, and merging the thrombus predictions obtained to obtain a set of thrombus segmentations.

14 Claims, 12 Drawing Sheets

(51) Int. Cl.
*G06T 7/12* (2017.01)
*G06T 15/00* (2011.01)
*G16H 30/40* (2018.01)

(52) U.S. Cl.
CPC ... *G16H 30/40* (2018.01); *G06T 2207/10088* (2013.01); *G06T 2207/20084* (2013.01); *G06T 2207/30016* (2013.01); *G06T 2207/30096* (2013.01)

(56) References Cited

U.S. PATENT DOCUMENTS

2023/0351586 A1* 11/2023 Brynolfsson ............. G06T 7/11
2024/0312008 A1* 9/2024 Kobold .................. G16H 30/40

OTHER PUBLICATIONS

International Search Report as issued in International Patent Application No. PCT/EP2022/068270, dated Nov. 9, 2022.
Kobold, J., et al., "Deep Learning for lesion and thrombus segmentation from cerebral MRI," Universite Paris Saclay, Dec. 2019, Retrieved from the Internet: URL:https://tel.archives-ouvertes.fr/tel-03592570/document, XP055902720, 161 pages.
Yu, Y., et al., "Use of Deep Learning to Predict Final Ischemic Stroke Lesions From Initial Magnetic Resonance Imaging," JAMA Network Open, Mar. 2020, XP055904828, Retrieved from the Internet: URL:https://jamanetwork.com/journals/jamanetworkopen/fullarticle/2762679, 13 pages.
Rekik I., et al., "Medical image analysis methods in MR/CT-imaged acute-subacute ischemic stroke lesion: Segmentation, prediction and insights into dynamic evolution simulation models. A critical appraisal," Neuroimage clinical, Jan. 2012, XP055904829, Retrieved from the Internet: URL:https://www.sciencedirect.com/science/article/pii/S2213158212000228/pdfft?md5=bf17ca317fddb4la080e636bl838f455&pid=I-s2.0-S2213158212000228-mainext.pdf, pp. 164-178.
Kobold, J., et al., "Logic LSTM for Segmentation of Thrombus and Lesion in Stroke MRI," Sep. 2019, 19 pages.
Kobold, J., et al., "Stroke Thrombus Segmentation on SWAN with Multi-Directional U-Nets," IEEE, (Year: 2019), 6 pages.

* cited by examiner

[Fig. 1]
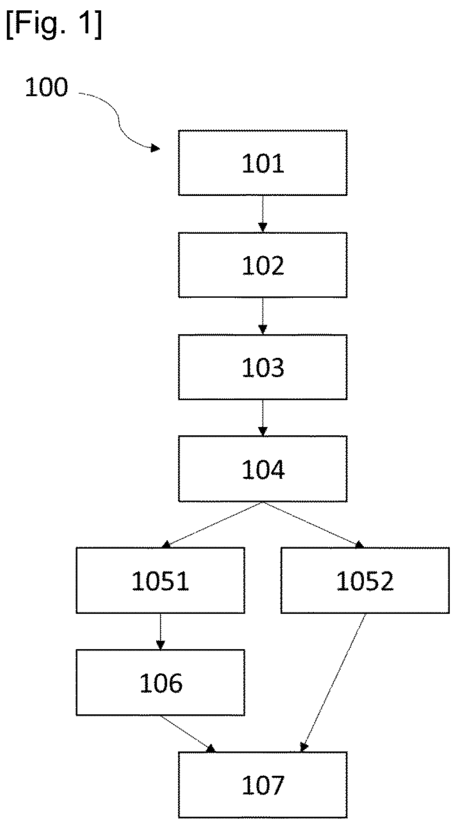

[Fig. 2]
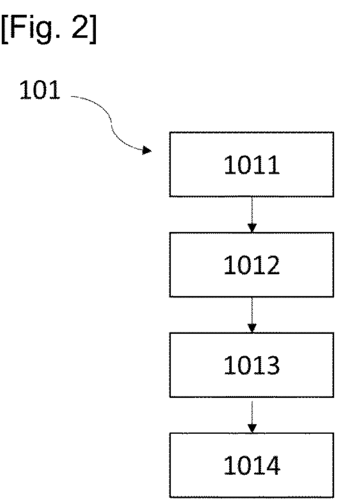

[Fig. 3]
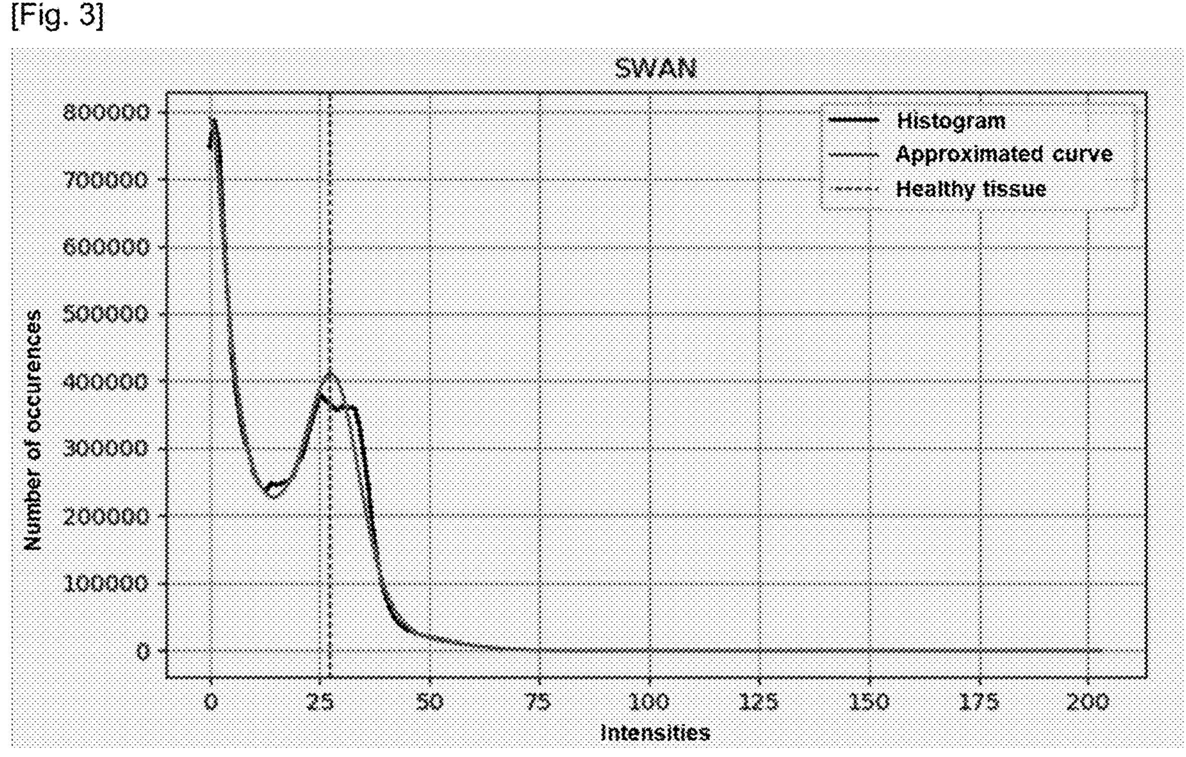

[Fig. 4]
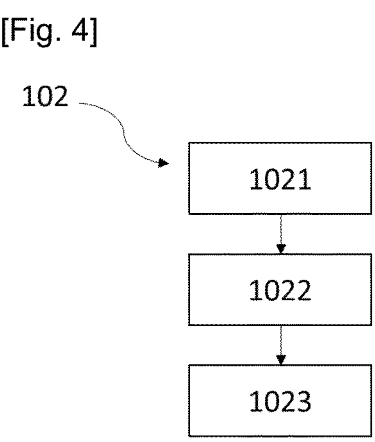

[Fig. 5]
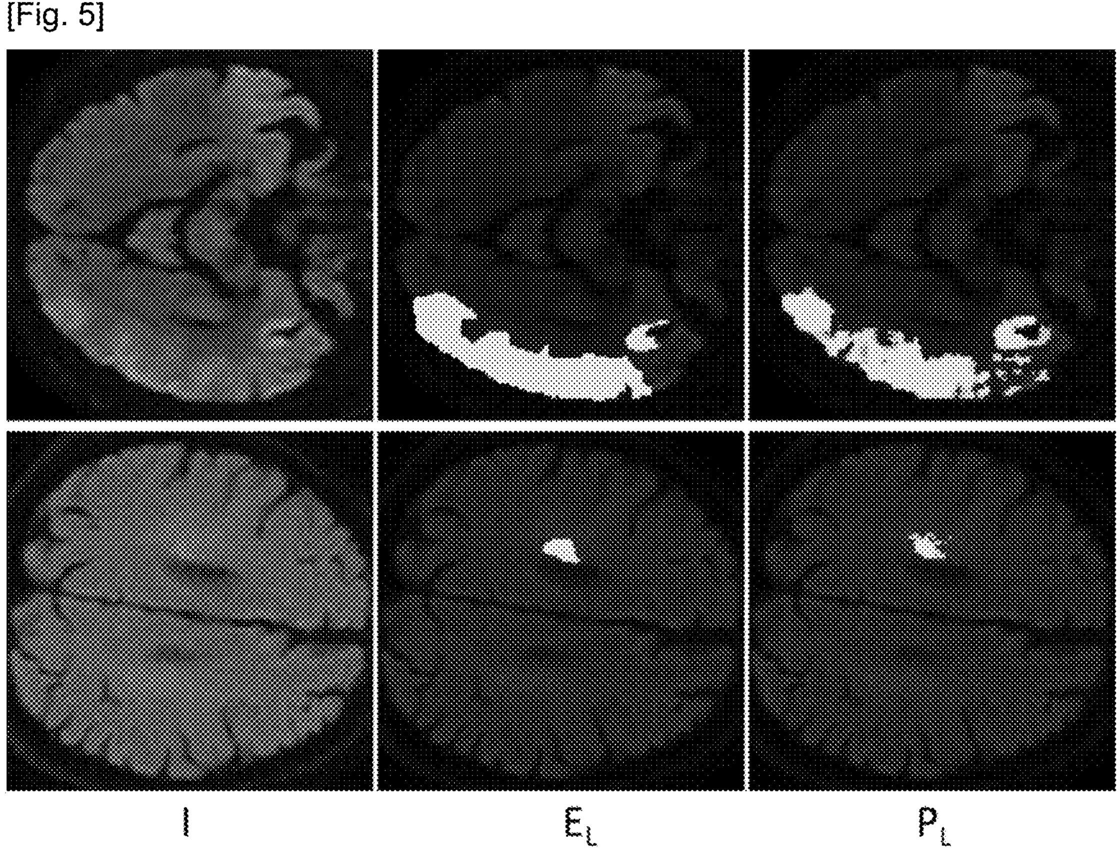

[Fig. 6]
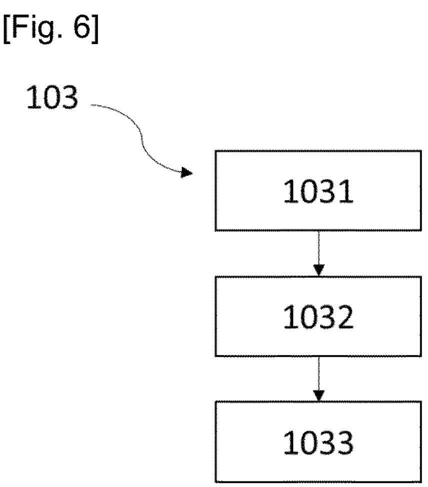

[Fig. 7]
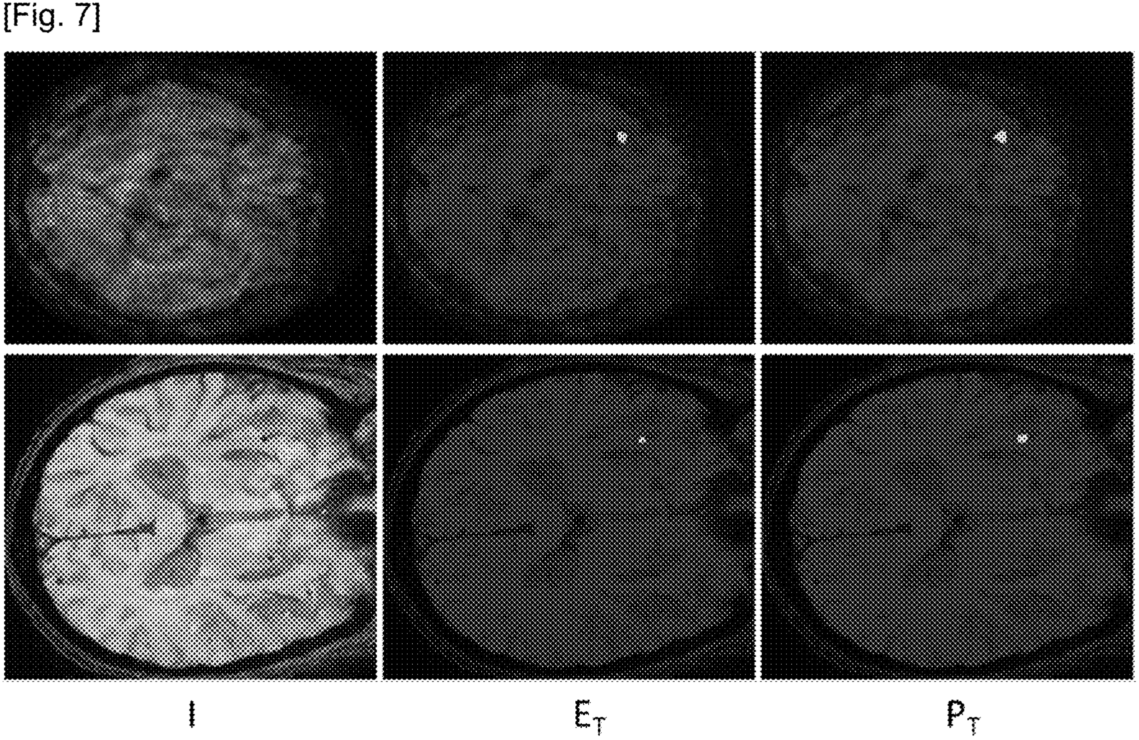

[Fig. 8]
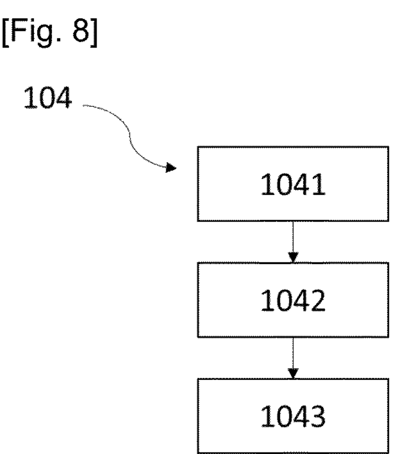

[Fig. 10]
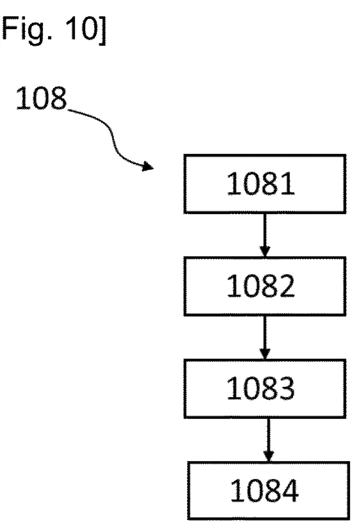

[Fig. 11]
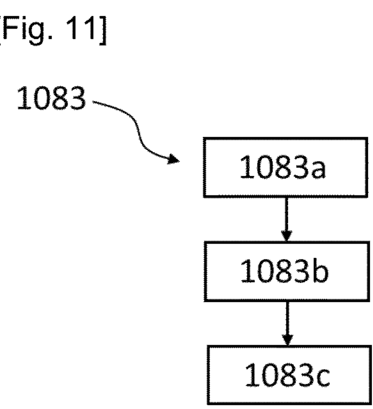

AUTOMATIC METHOD FOR SEGMENTATION OF A THROMBUS AND A LESION IN A THREE-DIMENSIONAL BRAIN IMAGE

CROSS-REFERENCE TO RELATED APPLICATIONS

This application is the U.S. National Stage of PCT/EP2022/068270, filed Jul. 1, 2022, which in turn claims priority to French patent application number 2107286 filed Jul. 6, 2021. The content of these applications are incorporated herein by reference in their entireties.

TECHNICAL FIELD OF THE INVENTION

The technical field of the invention is that of three-dimensional brain imaging, and more particularly that of the segmentation of a thrombus and a lesion in a three-dimensional brain image of a patient suffering from a cerebrovascular accident.

The present invention relates to a method for segmenting a thrombus and a lesion in a three-dimensional brain image and in particular to an automatic method for segmenting a thrombus and a lesion in a three-dimensional brain image. The present invention also relates to a computer program product and a recording medium.

TECHNOLOGICAL BACKGROUND OF THE INVENTION

A cerebrovascular accident or stroke corresponds either to obstruction of a brain artery by a blood clot or thrombus—this is known as an ischaemic stroke—or to rupture of a brain artery—this is known as a haemorrhagic stroke.

To limit the after-effects of a stroke, it is estimated that a maximum of 5 hours should elapse between the time the patient arrives at hospital and the time he or she is diagnosed and treated, the choice of treatment depending on the type of stroke diagnosed.

The diagnosis is conventionally made by an experienced healthcare professional on the basis of brain imaging by locating the thrombus and lesion caused by the thrombus. However, there are very few healthcare professionals capable of analysing brain images of stroke, and in practice the images often have to be sent from the hospital where the patient was admitted to another hospital with staff capable of analysing images. The time taken to obtain a diagnosis is then considerably increased and is often incompatible with the 5-hour maximum.

To remedy this problem, methods of segmenting the lesion or thrombus from a three-dimensional brain image have been developed. However, none of these methods is capable of detecting both the thrombus and the lesion in a reliable and fully automatic manner, that is with a detection rate of over 90% and a reduced number of false positives.

SUMMARY OF THE INVENTION

The invention offers a solution to the problems previously discussed, by proposing an automatic method for segmenting the thrombus and lesion in a brain image, with a detection rate greater than 90% and a reduced false positive rate.

A first aspect of the invention relates to an automatic method for segmenting a thrombus and a lesion caused by the thrombus in a three-dimensional brain image, the three-dimensional brain image being acquired according to at least one modality, each modality being associated with a set of images comprising a plurality of images each corresponding to a section of the three-dimensional image acquired according to the modality, along a sectional plane perpendicular to a given axis, the method including the following steps:

- supervised training of at least one primary recurrent artificial neural network configured to provide lesion prediction from an image, each primary recurrent artificial neural network being associated with a set of learning parameters and trained on a primary database including a plurality of brain images each associated with a set of information relating to the segmentation of each lesion in the image;
- supervised training of at least one secondary recurrent artificial neural network configured to provide thrombus prediction from an image, each secondary recurrent artificial neural network being associated with a set of training parameters and trained on a secondary database including a plurality of brain images each associated with a set of information relating to the segmentation of each thrombus in the image;
- using each trained primary recurrent artificial neural network, on each image of a primary set of images dependent on at least one set of images associated with a modality, and merging the lesion predictions obtained to obtain a set of lesion segmentations:
  - if the set of lesion segmentations includes at least one segmentation, selecting the segmentation with maximum volume as the lesion segmentation;
- using each trained secondary recurrent artificial neural network, on each image of a secondary set of images dependent on at least one set of images associated with a modality, and merging the thrombus predictions obtained to obtain a set of thrombus segmentations:
  - If the set of thrombus segmentations includes at least one segmentation, selecting the segmentation satisfying a proximity condition as the thrombus segmentation, the proximity condition depending on the lesion segmentation.

By virtue of the invention, at least one primary recurrent artificial neural network is trained and then used on a primary set of images obtained from the three-dimensional image in order to make lesion prediction per image of the primary set of images, and in parallel at least one secondary recurrent artificial neural network is trained and then used on a secondary set of images obtained from the three-dimensional image in order to make thrombus prediction per image of the secondary set of images.

The detection rate obtained by each primary recurrent artificial neural network is close to 100%, but the number of false positives is high.

When several primary recurrent artificial neural networks are used, lesion predictions obtained for all the primary recurrent artificial neural networks are then merged to obtain a set of lesion segmentations gathering the lesion segmentations most likely to coincide with the lesion in the three-dimensional image, taking account of the lesion predictions of each primary recurrent artificial neural network. Thus, by choosing different sets of training parameters and/or different brain images in the primary database and in the primary set of images for each primary recurrent artificial neural network, information used by each primary recurrent artificial neural network to make its lesion prediction is different and the choice of the lesion segmentation set is therefore based on more information, increasing its accuracy.

The lesion segmentation of the set of lesion segmentations with the largest volume is then selected as the effective lesion segmentation, which makes it possible to obtain a reduced number of false positives compared with prior art while maintaining a detection rate close to 100% for the lesion segmentation.

The detection rate obtained by each secondary recurrent artificial neural network is at least 89% and the number of false positives is high.

When several secondary recurrent artificial neural networks are used, the thrombus predictions obtained for all the secondary recurrent artificial neural networks are then merged to obtain a set of thrombus segmentations gathering the thrombus segmentations most likely to coincide with the thrombus in the three-dimensional image, taking account of the thrombus predictions of each secondary recurrent artificial neural network. Again, by choosing different sets of training parameters and/or different brain images in the secondary database and in the secondary set of images for each secondary artificial recurrent neural network, the choice of the set of thrombus segmentations is based on more information, which increases its accuracy.

The effective lesion segmentation is then used to select the effective thrombus segmentation from the thrombus segmentations in the set of thrombus segmentations, resulting in a detection rate greater than 90% and a reduced number of false positives compared to prior art for thrombus segmentation.

Once the segmentation of the lesion and the thrombus segmentation have been obtained, it is then possible to characterise the lesion or thrombus objectively by calculating numerical parameters, such as the volume, making interpretation of the three-dimensional image homogeneous, that is not dependent on the practitioner.

In addition to the characteristics just discussed in the preceding paragraph, the method according to the invention may have one or several additional characteristics from among the following, considered individually or according to any technically possible combinations.

According to one alternative embodiment, the three-dimensional image is acquired by MRI.

According to a first sub-alternative embodiment of the preceding alternative embodiment, the three-dimensional image is acquired by MRI according to a first susceptibility weighted angiography SWAN modality, a second phase of the radiofrequency signal of the phase susceptibility weighted angiography SWAN modality, a third time-of-flight ToF modality, a fourth Diffusion Weighted Images DWI modality and a fifth diffusion weighted images modality with exclusive application of the main magnetic field $B_o$.

According to a second sub-alternative embodiment of the preceding alternative embodiment compatible with the first sub-alternative embodiment, the method according to the invention includes a pre-processing step comprising the following sub-steps for each modality of the three-dimensional image:

- calculating a histogram on the grey levels of the voxels of the three-dimensional image acquired according to the modality;
- calculating a polynomial approximation of the logarithm of the histogram;
- application of the inverse function of the logarithm to the polynomial approximation to obtain an approximation of the histogram;
- determining a local maximum of the approximation of the histogram corresponding to healthy brain tissue and dividing the grey levels of the voxels of the three-dimensional image acquired according to the modality by the grey level corresponding to the local maximum in the histogram.

Thus, each three-dimensional image acquired by MRI is normalised to enable repeatable results to be obtained. Indeed, grey levels of the voxels in the three-dimensional images acquired by MRI vary between two patients or between two acquisitions carried out on a same patient, which does not allow automatic processing without normalisation beforehand.

According to one alternative embodiment of the first sub-alternative embodiment or of the second sub-alternative embodiment, the method according to the invention includes the following sub-steps of:

- for each image of the set of images associated with the fourth modality, subtracting, from the image considered, the corresponding image of the set of images associated with the fifth modality, to obtain a set of improved images;
- for each image of the set of images associated with the fourth modality, concatenating the image considered and the corresponding image of the set of improved images, to obtain a set of concatenated first images;
- for each image of the set of images associated with the first modality, concatenating the image considered, the corresponding image of the set of images associated with the second modality and the corresponding image of the set of images associated with the third modality, to obtain a set of concatenated second images.

According to one exemplary embodiment of the preceding alternative embodiment:

- the training step is performed for a first primary recurrent artificial neural network and a second primary recurrent artificial neural network associated with different sets of training parameters, on a same primary database including a plurality of concatenated first images;
- the use step is performed on a same primary set of images for the first primary recurrent artificial neural network and the second primary recurrent artificial neural network, the primary set of images corresponding to the set of concatenated first images;
- the training step is performed for a first secondary recurrent artificial neural network and a second secondary recurrent artificial neural network having identical sets of training parameters, on a first secondary database for the first secondary recurrent artificial neural network and on a second secondary database for the second secondary recurrent artificial neural network, the first secondary database including a plurality of images acquired according to the first modality, and the second secondary database including a plurality of concatenated second images;
- the use step is performed on a first secondary set of images for the first secondary recurrent artificial neural network and on a second secondary set of images for the second secondary recurrent artificial neural network, the first secondary set of images corresponding to the set of images associated with the first modality, and the second secondary set of images corresponding to the set of concatenated second images.

Thus, a detection rate of 100% and a reduced number of false positives compared with prior art is obtained for lesion segmentation and a detection rate of 93% and a reduced number of false positives compared with prior art is obtained for thrombus segmentation.

According to one alternative embodiment compatible with the preceding alternative embodiments, each primary recurrent artificial neural network and each secondary recurrent artificial neural network have the same architecture of the convolutional short- and long-term memory recurrent artificial neural network type having a memory, in which each convolution is replaced with a logic block in which a first part of an input piece of data passes through a convolutional layer and a second part of the input piece of data passes through a transfer block comprised of a transfer layer surrounded by two convolutional layers, the transfer layer performing several max-pooling operations with different window sizes.

Thus, each recurrent artificial neural network is translationally invariant and has a maximum receptive field and a reduced number of hyperparameters compared with conventional convolutional short- and long-term memory recurrent artificial neural networks.

According to one sub-alternative embodiment of the preceding alternative embodiment, the step of training a primary recurrent artificial neural network includes the following sub-steps for each image of the corresponding primary database:

- first submission of the image to the primary recurrent artificial neural network to fill its memory;
- second submission of the image to the primary recurrent neural network to provide lesion prediction from the memory filled, the second submission being immediately consecutive to the first submission;
- resetting the memory;

and the step of training a secondary recurrent artificial neural network includes the following sub-steps for each image in the corresponding secondary database:

- first submission of the image to the secondary recurrent artificial neural network to fill its memory;
- second submission of the image to the secondary recurrent neural network to provide a thrombus prediction from the memory filled, the second submission being immediately consecutive to the first submission;
- resetting the memory.

Thus, the prediction provided by each recurrent artificial neural network comes from a deep artificial neural network while the number of hyperparameters is reduced compared to conventional convolutional short and long term memory recurrent artificial neural networks.

According to another alternative embodiment compatible with the preceding alternative embodiments, the thrombus segmentation comprises a plurality of voxels identified as belonging to the thrombus, each voxel being associated with a false-positive label or with a true-positive label, the false-positive label or the true-positive label being assigned by the trained secondary recurrent artificial neural network, the method comprising a step of refining the thrombus segmentation comprising the following sub-steps:

- calculating the lesion envelope from the lesion segmentation,
- distributing the thrombus segmentation into a first set of voxels and a second set of voxels:
  - the first set of voxels includes the thrombus segmentation voxels associated with the false-positive label,
  - the second set of voxels includes the lesion segmentation voxels associated with the true-positive label,
- reducing the first set of voxels of the thrombus segmentation:
  - for each voxel of the first set of voxels, calculating the distance to the lesion, the distance to the lesion being the Euclidian distance of the voxel of the first set of voxels to the lesion envelope,
  - ordering the voxels in the first set of voxels as a function of the distance to the lesion calculated,
  - selecting a subset of voxels from the ordering of the voxels in the first set of voxels,
- selecting the segmentation corresponding to merging of the second set of voxels and the subset of voxels selected as the thrombus segmentation.

According to one sub-alternative of the preceding alternative embodiment, the step of selecting a subset of voxels is performed by selecting the N voxels of the first set of voxels having the smallest distance to the lesion, N being between 3 and 5.

According to another sub-variant of the preceding alternative embodiment, the step of selecting a subset of voxels is performed by selecting the voxels of the first set of voxels having a distance to the lesion less than a predetermined threshold.

Thus, it is possible to refine thrombus segmentation by reducing the number of false positives.

Advantageously, the method can comprise a step of volumetrically characterising the thrombus from the thrombus segmentation.

Still advantageously, the step of volumetrically characterising the thrombus may comprise the following sub-steps of:

- extracting the pixels of the thrombus segmentation from the thrombus segmentation, the pixels forming a point cloud contained in a volume, the volume being the maximum ellipsoidal envelope containing the thrombus,
- determining the geometric characteristics of the volume of the maximum ellipsoidal envelope containing the thrombus by principal component analysis of the point cloud along three main axes, the three main axes being orthogonal to each other,
- calculating the volume of the maximum ellipsoidal envelope containing the thrombus from the geometric parameters determined.

A second aspect of the invention relates to a computer program product comprising instructions which, when the program is executed on a computer, cause the same to implement the steps of the method according to the invention.

A third aspect of the invention relates to a computer-readable recording medium comprising instructions which, when executed by a computer, cause the same to implement the steps of the method according to the invention.

The invention and its different applications will be better understood upon reading the following description and upon examining the accompanying figures.

BRIEF DESCRIPTION OF THE FIGURES

The figures are set forth by way of indicating and in no way limiting purposes of the invention.

FIG. 1 is a block diagram illustrating the sequence of steps of a method according to the invention.

FIG. 2 is a block diagram illustrating the sequence of sub-steps of a first step of the method according to the invention.

FIG. 3 represents a histogram of the grey levels of a three-dimensional brain image.

FIG. 4 is a block diagram illustrating the sequence of sub-steps of a second step of the method according to the invention.

FIG. 5 shows a first example at the top and a second example at the bottom including, from left to right, a brain image, a lesion to be identified in the image and a lesion prediction provided by the method according to the invention from the image.

FIG. 6 is a block diagram illustrating the sequence of sub-steps of a third step of the method according to the invention.

FIG. 7 shows a first example at the top and a second example at the bottom including, from left to right, a brain image, a thrombus to be identified in the image and a thrombus prediction provided by the method according to the invention from the image.

FIG. 8 is a block diagram illustrating the sequence of sub-steps of a fourth step of the method according to the invention.

FIG. 9 is a block diagram illustrating the sequence of an eighth and a ninth step of the method according to the invention.

FIG. 10 is a block diagram illustrating the sequence of sub-steps of the eighth step of the method according to the invention.

FIG. 11 is a block diagram illustrating the sequence of the sub-steps of the third sub-step of the eighth step of the method according to the invention.

FIG. 12 is a block diagram illustrating the sequence of the sub-steps of the ninth step of the method according to the invention.

DETAILED DESCRIPTION

Unless otherwise specified, a same element appearing in different figures has a single reference.

The invention relates to an automatic method for segmenting a thrombus and a lesion in a three-dimensional brain image of a patient, the thrombus having caused a brain lesion leading to a cerebrovascular accident or stroke in the patient.

By "segmenting an element in a three-dimensional image", it is meant identifying each voxel of the image belonging to the element, a voxel being defined as a three-dimensional pixel.

The three-dimensional image is acquired by an imaging system according to one or several modalities, otherwise called sequences, each having different acquisition parameters.

The three-dimensional image is acquired, for example, by X-ray scanner or by Magnetic Resonance Imaging or MRI.

If the three-dimensional image is acquired by an MRI sequence or combination of sequences, it may for example be acquired using at least one of the following methods: an Echo Planar Image (EPI) sequence, a Diffusion Weighted Images (DWI) sequence, a Fluid Attenuated Inversion Recovery (FLAIR) sequence, a Time of Flight (ToF) sequence, a Susceptibility Weighted Angiography (SWAN) sequence, a Susceptibility-Weighted Images (SWI) sequence, a diffusion weighted images DWI sequence with application of the main magnetic field $B_o$ only, that is with a degree of diffusion weighting equal to 0, or a phase sequence of the radiofrequency signal of the susceptibility weighted angiography SWAN.

For each modality, a set of images is obtained from the three-dimensional image acquired according to the modality, the set of images including a plurality of images each corresponding to a section of the three-dimensional image acquired according to the modality, along a sectional plane perpendicular to a given axis.

The sectional planes of the images of a set of images are parallel to each other and not coincident, that is the sectional planes are spaced apart along the axis to which they are perpendicular, and can each be associated with a position on the axis.

The axis is transverse, for example.

The sectional planes are identical for each modality, that is each set of images has the same number of images and each image in one set of images has a corresponding image in each other set of images.

Each image in the set of images can then be partitioned into thumbnails having reduced dimensions. The size of the thumbnails is, for example, chosen so that each thumbnail has an coverage zone with at least one other thumbnail.

For example, each image is partitioned into a number of thumbnails of between about ten and a hundred thumbnails.

[FIG. 1] FIG. 1 is a block diagram illustrating the sequence of steps of the method 100 according to the invention.

The method 100 according to the invention may include a first pre-processing step 101 if the three-dimensional brain image has been acquired by MRI.

The first step 101 is then performed for each modality of the three-dimensional MRI image.

[FIG. 2] FIG. 2 is a block diagram illustrating the sequence of sub-steps of the first step 101 of the method 100.

A first sub-step 1011 of the first step 101 consists in calculating a histogram of the grey levels or intensities of the voxels of the three-dimensional MRI image acquired according to the modality.

[FIG. 3] FIG. 3 is an example of a histogram of the grey levels of a three-dimensional brain image.

In FIG. 3, the histogram has a global maximum in proximity to grey level 0 and a local maximum around grey level 25.

The local maximum with a number of occurrences of 400,000 corresponds to healthy brain tissue in the three-dimensional MRI image.

A second sub-step 1012 of the first step 101 consists in calculating a polynomial approximation of the logarithm of the histogram calculated in the first sub-step 1011.

A third sub-step 1013 of the first step 101 consists in applying the inverse function of the logarithm to the polynomial approximation obtained in the second sub-step 1012 to obtain an approximation of the histogram.

FIG. 3 also represents the approximation of the histogram.

A fourth sub-step 1014 of the first step 101 consists in determining local maximum of the approximation of the histogram corresponding to the healthy brain tissue.

The local maximum is determined, for example, by thresholding on the number of occurrences.

The fourth sub-step 1014 of the first step 101 then consists in dividing the grey level of each voxel of the three-dimensional MRI image acquired according to the modality, by the grey level corresponding to the local maximum in the histogram.

In FIG. 3, the fourth sub-step 1014 amounts to dividing the grey level of each voxel of the three-dimensional MRI image acquired according to the modality by approximately 25.

The method 100 according to the invention may include a second processing step 102 if the three-dimensional brain image has been acquired by MRI according to a first susceptibility weighted angiography SWAN modality, a second phase of the radiofrequency signal of the susceptibility weighted angiography SWAN phase modality, a third time-of-flight ToF modality, a fourth diffusion weighted images DWI modality and a fifth diffusion weighted images DWI modality with exclusive application of the main magnetic field $B_o$.

For example, the first step 101 has been performed beforehand on each of the five preceding modalities.

[FIG. 4] FIG. 4 is a block diagram illustrating the sequence of sub-steps of the second step 102 of the method 100.

A first sub-step 1021 of the second step 102 consists in obtaining a set of improved images by subtracting from each image I of the set of images associated with the fourth modality, the corresponding image I of the set of images associated with the fifth modality.

The set of improved images therefore contains as many images as each set of images.

By "subtracting a first image from a second image», it is meant subtracting, for each pixel, the grey level of the pixel of the first image from the grey level of the pixel of the corresponding second image.

A second sub-step 1022 of the second step 102 consists in obtaining a set of concatenated first images by concatenating each image I of the set of images associated with the fourth modality with the corresponding image I of the set of improved images obtained in the first sub-step 1021.

The set of concatenated first images thus contains as many images as each set of images.

By "image resulting from the concatenation of a first image and a second image», it is meant a single image gathering the first image and the second image.

A third sub-step 1023 of the second step 102 consists in obtaining a set of concatenated second images by concatenating each image I of the set of images associated with the first modality, with the corresponding image I of the set of images associated with the second modality and with the corresponding image I of the set of images associated with the third modality.

The set of concatenated second images thus contains as many images as each set of images.

A third step 103 of the method 100 consists in training, in a supervised manner, at least one primary recurrent artificial neural network on a primary database in order to obtain a primary recurrent artificial neural network trained capable of providing, from an image, a lesion prediction coinciding with the lesion actually present in the image.

A lesion prediction corresponds to a probability map associating with each pixel of the image a probability that the pixel is included in a lesion. Only pixels associated with a probability greater than a threshold are considered to actually belong to a lesion.

The threshold is, for example, 0.5.

Each primary recurrent artificial neural network may be trained on a same primary database or on a different primary database with respect to the other primary recurrent artificial neural networks.

Supervised training, otherwise known as supervised learning, makes it possible to train an artificial neural network for a predefined task, by updating its hyperparameters so as to minimise a cost function corresponding to the error between the output piece of data provided by the artificial neural network and the true output piece of data, that is what the artificial neural network should provide as output in order to fulfil the predefined task on some input piece of data.

A training database therefore includes input data, each associated with a true output data.

Each primary database includes a plurality of brain images each associated with a set of information relating to the segmentation of each lesion in the image.

Thus, the input data are the brain images and the true output data are the information relating to the segmentation of each lesion in the image.

[FIG. 5] FIG. 5 shows a first example at the top and a second example at the bottom, of a brain image I, of information $E_L$ relating to the segmentation of a lesion in the image I and a lesion prediction $P_L$ provided by the primary recurrent artificial neural network.

Supervised training of each primary recurrent artificial neural network therefore consists in updating the hyperparameters so as to minimise a cost function corresponding to the error between the lesion prediction provided by the primary recurrent artificial neural network from a brain image I in the primary database and the information relating to the segmentation of each lesion in the image I associated with the image I in the primary database.

The cost function is, for example, the cross-entropy function.

Each primary recurrent artificial neural network is associated with a set of learning parameters which may be identical to or different from the sets of parameters of the other primary recurrent artificial neural networks.

The set of learning parameters includes, for example, the number of images per iteration and the dimensions of the images used during training.

Each primary recurrent artificial neural network is, for example, an LSTM (Long-Short Term Memory) recurrent artificial neural network and therefore has a memory, or a convolutional LSTM network, or even a maximum receptive field convolutional LSTM network.

By "receptive field of an artificial neural network», it is meant that part of the input piece of data which is accessible through the last layer of the artificial neural network in order to make its prediction.

A maximum receptive field convolutional LSTM network is, for example, a convolutional LSTM artificial neural network in which each convolution is replaced with a logic block whose receptive field is as large as the input piece of data. In the logic block, a first part of the input piece of data passes through a convolutional layer and a second part of the input piece of data passes through a transfer block comprised of a transfer layer surrounded by two convolutional layers, the transfer layer performing several max-pooling operations with different window sizes.

Each primary recurrent artificial neural network may have an architecture that is identical to or different from the architecture of the other primary recurrent artificial neural networks.

The third step 103 of the method 100 is carried out, for example, for a first primary recurrent artificial neural network and a second primary recurrent artificial neural network having a same maximum perceptive field convolutional LSTM type architecture and different sets of training parameters, on a same primary database including a plurality of first images I concatenated as brain images I.

[FIG. 6] FIG. 6 is a block diagram illustrating the sequence of sub-steps of the third step 103 of the method 100.

The third step 103 may include a first sub-step 1031, a second sub-step 1032 and a third sub-step 1033 for each image I of the primary database.

The first sub-step 1031 consists in subjecting the image I a first time to the primary recurrent artificial neural network which will thus fill its memory.

The second sub-step 1032 consists in subjecting the image I a second time to the primary recurrent artificial neural network which will thus provide lesion prediction $P_L$ using the information stored in its memory in the first sub-step 1031.

The second submission is immediately consecutive to the first sub-submission, that is no other image I is subjected to the primary recurrent artificial neural network between the first sub-step 1031 and the second sub-step 1032.

The third substep 1033 consists in clearing the memory of the primary recurrent artificial neural network.

A fourth step 104 of the method 100 consists in training, in a supervised manner, at least one secondary recurrent artificial neural network on a secondary database to obtain a secondary recurrent artificial neural network trained capable of providing, from an image I, a thrombus prediction coinciding with the thrombus actually present in the image.

Each secondary recurrent artificial neural network may be trained on a same secondary database or on a different secondary database with respect to the other secondary recurrent artificial neural networks.

Each secondary database includes a plurality of brain images I each associated with a set of information relating to the segmentation of each thrombus in the image.

Thus, the input data are the brain images I and the true output data are the information relating to the segmentation of each thrombus in the image.

[FIG. 7] FIG. 7 shows a first example at the top and a second example at the bottom, of a brain image I, of information $E_T$ relating to the segmentation of a thrombus in the image I and a thrombus prediction $P_T$ provided by the secondary recurrent artificial neural network.

The supervised training of each secondary recurrent artificial neural network therefore consists in updating the hyperparameters so as to minimise a cost function corresponding to the error between the thrombus prediction provided by the secondary recurrent artificial neural network from a brain image I in the secondary database and the information relating to the segmentation of each thrombus in the image I associated with the image I in the secondary database.

The cost function is, for example, the cross-entropy function.

Each secondary recurrent artificial neural network is associated with a set of learning parameters which may be identical to or different from the sets of parameters of the other secondary recurrent artificial neural networks.

The dimensions of the images used when training the set of learning parameters of each primary recurrent artificial neural network are, for example, larger than the dimensions of the images used when training the set of learning parameters of each secondary recurrent artificial neural network.

Each secondary recurrent artificial neural network is for example an LSTM network, or a convolutional LSTM network, or a maximum receptive field convolutional LSTM network.

Each secondary recurrent artificial neural network may have an architecture that is identical to or different from the architecture of the other secondary recurrent artificial neural networks.

Each secondary recurrent artificial neural network may have an architecture that is identical to or different from the architecture of the primary recurrent artificial neural networks.

For example, each primary recurrent artificial neural network and each secondary recurrent artificial neural network have a same architecture of the maximum receptive field convolutional LSTM network type.

The fourth step 104 of the method 100 is carried out, for example, for a first secondary recurrent artificial neural network and a second secondary recurrent artificial neural network having the same maximum perceptive field convolutional LSTM type architecture and identical sets of training parameters, on a first secondary database for the first secondary recurrent artificial neural network and on a second secondary database different from the first secondary database for the second secondary recurrent artificial neural network, the first secondary database including a plurality of images I acquired according to the first modality as brain images I and the second secondary database including a plurality of second images I concatenated as brain images I.

[FIG. 8] FIG. 8 is a block diagram illustrating the sequence of sub-steps of the fourth step 104 of the method 100.

The fourth step 104 may include a first sub-step 1041, a second sub-step 1042 and a third sub-step 1043 for each image I in the secondary database.

The first sub-step 1041 consists in subjecting the image I a first time to the secondary recurrent artificial neural network which will thus fill its memory.

The second sub-step 1042 consists in subjecting the image I a second time to the secondary recurrent artificial neural network, which then provides a thrombus prediction $P_T$ using the information stored in its memory in the first sub-step 1041.

The second submission is immediately consecutive to the first submission, that is no other image I is subjected to the secondary recurrent artificial neural network between the first sub-step 1041 and the second sub-step 1042.

The third substep 1043 consists in clearing memory of the secondary recurrent artificial neural network.

The fourth step 104 could also be performed prior to or in parallel with the third step 103.

A fifth step 105 of the method 100 according to the invention includes a first sub-step 1051 and a second sub-step 1052 which may be performed in parallel as illustrated in FIG. 1 or one after the other.

The first sub-step 1051 consists in using each primary recurrent artificial neural network trained in the third step 103, on each image I of a primary set of images, each primary recurrent artificial neural network then providing a lesion prediction $P_L$ for each image I of the primary set of images.

Each primary recurrent artificial neural network may be used on a same or a different primary set of images relative to the other primary recurrent artificial neural networks.

Each primary set of images depends on at least one set of images associated with a modality, that is each primary set of images may correspond to a set of images or a combination of set of images.

The first sub-step 1051 is for example performed on a same primary set of images for the first primary recurrent artificial neural network and the second primary recurrent artificial neural network previously described, and the primary set of images corresponds to the set of concatenated first images obtained in the second step 102.

The first sub-step 1051 then consists in obtaining a set of lesion segmentations by merging the lesion predictions $P_L$ obtained for the set of primary recurrent artificial neural networks.

Thus, if two primary recurrent artificial neural networks are used, the lesion predictions $P_L$ by the first primary recurrent artificial neural network are merged with the lesion predictions $P_L$ by the second primary recurrent artificial neural network.

Merging is for example performed by multiplying each lesion prediction $P_L$ obtained for an image I of a first primary set of images provided by a first primary recurrent artificial neural network with the lesion prediction $P_L$ obtained for a corresponding image I of another primary set of images for each other primary recurrent artificial neural network.

A merging probability map is then obtained for each image of the first primary set of images, in which each pixel is associated with the product of the probabilities associated with the corresponding pixel in each lesion prediction $P_L$ provided for image I.

Merging then consists in applying a threshold to each merging probability map to retain only those pixels associated with a probability greater than the threshold in the merging probability map.

The threshold is equal to 0.25, for example.

By comparing the groups of neighbouring pixels in each thresholded merging probability map taking account of the position of the corresponding image I along the axis perpendicular to the corresponding sectional plane, groups of neighbouring voxels can be determined, each group of neighbouring voxels then constituting a lesion segmentation which is placed in the set of lesion segmentations.

If at the end of the first sub-step 1051 of the fifth step 105, the set of segmentations is empty, it is considered that the image contained no lesion.

Otherwise, that is if at the end of the first sub-step 1051 of the fifth step 105 the set of segmentations includes at least one lesion segmentation, a sixth step 106 of the method 100 is performed.

The second substep 1052 consists in using each secondary recurrent artificial neural network trained in the fourth step 104, on each image I of a secondary set of images, each secondary recurrent artificial neural network then providing a thrombus prediction $P_T$ for each image of the secondary set of images.

Each secondary recurrent artificial neural network may be used on the same or a different secondary set of images with respect to the other secondary recurrent artificial neural networks.

Each secondary set of images depends on at least one set of images associated with a modality.

The second sub-step 1052 is performed, for example, on a first secondary set of images for the first secondary recurrent artificial neural network previously described and on a second secondary set of images for the second secondary recurrent artificial neural network previously described, the first secondary set of images corresponding to the set of images associated with the first modality, and the second secondary set of images corresponding to the set of concatenated second images obtained in the second step 102.

The second sub-step 1052 then consists in obtaining a set of thrombus segmentations by merging the thrombus predictions $P_T$ obtained for the set of secondary recurrent artificial neural networks.

Thus, if two secondary recurrent artificial neural networks are used, the thrombus predictions $P_T$ by the first secondary recurrent artificial neural network are merged with the thrombus predictions $P_T$ by the second secondary recurrent artificial neural network.

Merging is for example performed by multiplying each thrombus prediction $P_T$ obtained for an image I of a first secondary set of images provided by a first secondary recurrent artificial neural network with the thrombus prediction $P_T$ obtained for a corresponding image I of another secondary set of images for each other secondary recurrent artificial neural network.

A merging probability map is then obtained for each image of the first secondary set of images, in which each pixel is associated with the product of the probabilities associated with the corresponding pixel in each thrombus prediction $P_T$ provided for image I.

Merging then consists in applying a threshold to each merging probability map to retain only those pixels associated with a probability greater than the threshold in the merging probability map.

The threshold is, for example, 0.25.

By comparing the groups of neighbouring pixels in each thresholded merging probability map as a function of the position of the corresponding images I along the axis perpendicular to the corresponding sectional plane, groups of neighbouring voxels can be determined, each group of neighbouring voxels then constituting a thrombus segmentation which is placed in the set of thrombus segmentations.

The sixth step 106 of the method 100 according to the invention consists in selecting, as the segmentation of the lesion in the three-dimensional image, the segmentation of the set of lesion segmentations with maximum volume, that is comprising the largest number of voxels.

A seventh step 107 of the method 100 according to the invention consists in selecting, as the thrombus segmentation in the three-dimensional image, the segmentation of the set of thrombus segmentations satisfying a proximity condition dependent on the segmentation of the lesion obtained in the sixth step 106.

For example, a thrombus segmentation satisfies a proximity condition if its position in the images I lies between the position of the lesion in the image I and the bottom of the patient's head.

By performing all the steps of the method 100 described in FIG. 1 using the first primary recurrent artificial neural network, the second primary recurrent artificial neural network, the first secondary recurrent artificial neural network and the second secondary recurrent artificial neural network previously described, a detection rate of 100% and a reduced number of false positives are obtained for lesion segmentation and thrombus segmentation.

It is possible to further reduce the number of false positives by performing an eighth step 108 of post-processing the thrombus segmentation obtained at the end of method 100. This step 108 is illustrated in FIGS. 10 to 11.

By false-positives, it is meant voxels in the thrombus segmentation which are associated with a high probability of not belonging to the thrombus. Conversely, true-positives are voxels in the thrombus segmentation that are associated with a high probability of belonging to the thrombus. These probabilities are determined upon training the secondary recurrent artificial neural network. Thus, in step 107 of the method 100, the use of each secondary recurrent artificial neural network makes it possible to associate a false-positive or true-positive label with each voxel of the thrombus segmentation.

Step 108 consists in excluding from the thrombus segmentation a number of false positives as a function of their distance to the already segmented lesion 106.

For this, a first sub-step 1081 consists in calculating the lesion envelope from the lesion segmentation determined in step 106.

A second sub-step 1082 consists in distributing the thrombus segmentation 107 into two sets of voxels: the first set of voxels FP includes all the voxels of the thrombus segmentation associated with the false-positive label and the second set of voxels VP includes all the voxels associated with the true-positive label, that is the second set includes all the voxels of the thrombus segmentation which do not belong to the first set of voxels FP.

Starting from the first set of voxels FP, a third sub-step 1083 of reducing number of false positives is performed.

A first sub-sub-step 1083*a* consists in calculating, for each voxel of the first set of voxels FP, Euclidean distance from the voxel to the lesion envelope. Thus, each voxel in the first set of voxels FP is associated with a parameter giving its distance from the lesion.

A second sub-sub-step 1083*b* consists in ordering, in ascending order for example, the voxels of the first set of voxels FP as a function of the distance to the lesion previously calculated. A list of voxels ordered according to their distance to the lesion is thus obtained.

In a third sub-sub-step 1083*c*, only a number of voxels of the first set of voxels FP are selected from the ordered list of voxels to form a subset of voxels FPR of the first set of voxels FP. The voxels in the subset of voxels FPR are therefore a reduced set of false-positive voxels.

The selection of voxels from the ordered list of voxels can be performed in several ways. In one way, the 3 to 5 voxels in the ordered voxel list with the smallest distance to the lesion can be selected. Another way is to select the voxels from the list of ordered voxels that are associated with a distance to the lesion that is less than a predetermined threshold. This threshold may be 1 to 2 units.

Finally, step 108 comprises a fourth sub-step 1084 consisting in joining the subset of voxels FPR and the second set of voxels VP to form the thrombus segmentation, this being a thrombus segmentation refined with respect to the thrombus segmentation determined in step 107. The false positive rate is indeed reduced.

Once the lesion segmentation and segmentation thrombus have been obtained, it is then possible to characterise the lesion or thrombus objectively by calculating numerical parameters, such as the volume, so as to provide the practitioner with an image that can be interpreted in a homogeneous manner, that is with little dependence on the practitioner.

In particular, the volume and shape of the thrombus provide the practitioner with vital additional information in that they help the practitioner to make diagnosis and guide the treatment to be given. Indeed, depending on whether the thrombus occupies a large or small volume, and/or whether its shape is elliptical or substantially spherical, the treatment protocol to be applied will be different.

Figure 9:
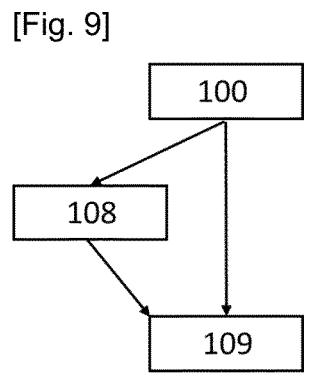

For this, the method 100 may be followed by a ninth step 109 of volumetrically characterising the already segmented thrombus. As illustrated in FIG. 9, which is a block diagram illustrating the sequence of an eighth and a ninth step 108, 109 in the method 100, step 109 may be carried out either from the thrombus segmentation obtained at the end of the method 100, or from the refined thrombus segmentation obtained in step 108.

Volumetrically characterising the thrombus means calculating the volume of the maximum ellipsoidal envelope containing the thrombus and calculating the geometric parameters characterising this volume. Thus, considering a simple volume of ellipsoidal shape, the geometric parameters determined in step 109 will be the lengths, respectively, of the long half-axis, the medium half-axis and the small half-axis. These values make it possible to characterise shape of the volume objectively.

Figure 12:
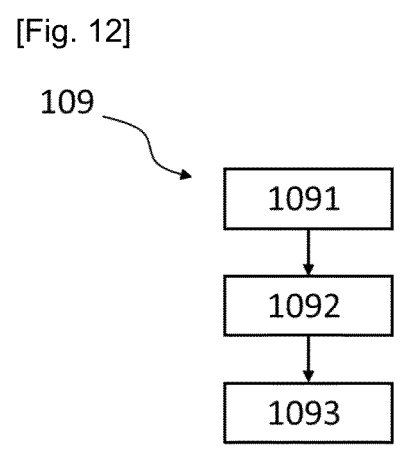

With reference to FIG. 12, volumetrically characterising the thrombus (109) is carried out in at least three steps 1091, 1092 and 1093.

The first sub-step 1091 consists in extracting from the thrombus segmentation 107 or 108 the n pixels which form the thrombus, n being greater than 3. More precisely, step 1091 consists in extracting, for all the voxels of the thrombus segmentation, the 3 pixels corresponding to the three spatial directions of each voxel, and in organising the n pixels extracted in a list. This list takes the form, for example, of a matrix M having the spatial coordinates of each pixel arranged in rows.

The n pixels extracted form a 3D point cloud contained in a volume, for example in an ellipsoidal volume. This volume represents the maximum ellipsoidal envelope containing the thrombus.

The second sub-step 1092 of step 109 consists in calculating the geometric parameters characterising the volume of the maximum ellipsoidal envelope containing the thrombus. Considering a volume of ellipsoidal shape, the geometric parameters characterising the volume of the maximum ellipsoidal envelope containing the thrombus are the lengths of the long, medium and small half-axes of the ellipsoid.

For this, in sub-step 1092, the 3D point cloud formed by the n extracted pixels is principal component analysed taking 3 orthogonal axes as the main axes, these orthogonal axes defining the axes of the ellipsoid. In other words, principal component analysis is used to determine the three orthogonal axes that best represent the 3D point cloud, that is the volume of the maximum ellipsoidal envelope containing the thrombus.

More precisely, the Karhunen-Loeve theorem, comprising the steps of matrix diagonalization, eigenvector transformation and principal component analysis, can be used on the matrix M determined in substep 1091.

The matrix M' is thus determined, this matrix being the transpose of the matrix M.

The matrix product M×M' is then decomposed into the sum of three matrices $M_1$, $M_2$ and $M_3$ having the same dimension as M:

$$M \times M' = l_1 \times M_1 + l_2 \times M_2 + l_3 \times M_3,$$

$M_i = u_i \times u_j$, with i=1, 2, 3 and j=1, 2, 3, and $(u_i, l_i)$ forms the eigenvalue/vector pair, and $l_1 > l_2 > l_3$.

Geometrically, $l_i$ is a half-axis of the ellipsoid.

The third sub-step 1093 of step 109 consists in calculating the volume V of the maximum ellipsoidal envelope containing the thrombus from the half-axes $l_i$ determined in step 1092. The volume V is given by the following formula:

$$V = \frac{4}{3}\pi(l_1 \times l_2 \times l_3).$$

In summary, at the end of step 109 the geometrical parameters of greater length $l_1$, medium length $l_2$ and small length $l_3$ characterising the volume of the maximum ellipsoidal envelope containing the thrombus, as well as the volume of the maximum ellipsoidal envelope containing the thrombus are obtained.

The invention claimed is:

1. An automatic method for segmenting a thrombus and a lesion generated by the thrombus in a three-dimensional brain image, the three-dimensional brain image being acquired according to at least one modality, each modality being associated with a set of images comprising a plurality of images each corresponding to a section of the three-dimensional image acquired according to the modality, along a sectional plane perpendicular to a given axis, the method comprising:

supervised training of at least one primary recurrent artificial neural network configured to provide lesion prediction from an image, each primary recurrent artificial neural network being associated with a set of training parameters and trained on a primary database including a plurality of brain images each associated with a set of information relating to the segmentation of each lesion in the image;

supervised training of at least one secondary recurrent artificial neural network configured to provide a thrombus prediction from an image, each secondary recurrent artificial neural network being associated with a set of learning parameters and trained on a secondary database including a plurality of brain images each associated with a set of information relating to the segmentation of each thrombus in the image;

using each primary recurrent artificial neural network trained, on each image of a primary set of images dependent on at least one set of images associated with a modality, and merging the lesion predictions obtained to obtain a set of lesion segmentations:

if the set of lesion segmentations includes at least one segmentation, selecting the segmentation with the maximum volume as the lesion segmentation;

using each secondary recurrent artificial neural network trained, on each image of a secondary set of images dependent on at least one set of images associated with a modality, and merging the thrombus predictions obtained to obtain a set of thrombus segmentations:

if the set of thrombus segmentations includes at least one segmentation, selecting the segmentation satisfying a proximity condition as the thrombus segmentation, the proximity condition depending on the lesion segmentation.

2. The method according to claim 1, wherein the three-dimensional image is acquired by MRI.

3. The method according to claim 2, wherein the three-dimensional image is acquired by MRI according to a first susceptibility weighted angiography SWAN modality, a second phase modality of the radiofrequency signal of the susceptibility weighted angiography SWAN, a third time-of-flight ToF modality, a fourth diffusion weighted images DWI modality and a fifth diffusion weighted images DWI modality with exclusive application of the main magnetic field $B_o$.

4. The method according to claim 2, including a pre-processing step comprising the following sub-steps for each modality of the three-dimensional image:

calculating a histogram on the grey levels of the voxels of the three-dimensional image acquired according to the modality;

calculating a polynomial approximation of the logarithm of the histogram;

applicating the inverse function of the logarithm to the polynomial approximation to obtain an approximation of the histogram;

determining a local maximum of the approximation of the histogram corresponding to healthy brain tissue and dividing the grey levels of the voxels of the three-dimensional image acquired according to the modality by the grey level corresponding to the local maximum in the histogram.

5. The method according to claim 3, including a processing step comprising the following sub-steps:

for each image of the set of images associated with the fourth modality, subtracting, from the image considered, the corresponding image of the set of images associated with the fifth modality, to obtain a set of improved images;

for each image of the set of images associated with the fourth modality, concatenating the image considered and the corresponding image of the set of improved images, to obtain a set of concatenated first images;

for each image of the set of images associated with the first modality, concatenating the image considered, the corresponding image of the set of images associated with the second modality and of the corresponding image of the set of images associated with the third modality, to obtain a set of concatenated second images.

6. The method according to claim 5, wherein:

the supervised training of at least one primary recurrent artificial neural network is performed for a first primary recurrent artificial neural network and a second primary recurrent artificial neural network associated with different sets of training parameters, on a same primary database including a plurality of concatenated first images;

the using of each primary recurrent artificial neural network trained is performed on a same primary set of images for the first primary recurrent artificial neural network and the second primary recurrent artificial neural network, the primary set of images corresponding to the set of concatenated first images;

the supervised training of at least one secondary recurrent artificial neural network is performed for a first secondary recurrent artificial neural network and a second secondary recurrent artificial neural network having identical sets of training parameters, on a first secondary database for the first secondary recurrent artificial neural network and on a second secondary database for the second secondary recurrent artificial neural network, the first secondary database including a plurality of images acquired according to the first modality and the second secondary database including a plurality of concatenated second images;

the using of each secondary recurrent artificial neural network trained is performed on a first secondary set of images for the first secondary recurrent artificial neural network and on a second secondary set of images for the second secondary recurrent artificial neural network, the first secondary set of images corresponding to the set of images associated with the first modality and the second secondary set of images corresponding to the set of concatenated second images.

7. The method according to claim 1, wherein each primary recurrent artificial neural network and each secondary recurrent artificial neural network have the same architecture of the convolutional short-and long-term memory recurrent artificial neural network type having a memory, wherein each convolution is replaced with a logic block in which a first part of an input piece of data passes through a convolutional layer and a second part of the input piece of data passes through a transfer block comprised of a transfer layer surrounded by two convolutional layers, the transfer layer performing several max-pooling operations with different window sizes.

8. The method according to claim 7, wherein the training of a primary recurrent artificial neural network includes the following substeps for each image of the corresponding primary database:

first submission of the image to the primary recurrent artificial neural network to fill its memory;

second submission of the image to the primary recurrent neural network to provide lesion prediction from the memory filled, the second submission being immediately consecutive to the first submission;

resetting the memory;

and the step of training a secondary recurrent artificial neural network includes the following sub-steps for each image of the corresponding secondary database:

first submission of the image to the secondary recurrent artificial neural network to fill its memory;

second submission of the image to the secondary recurrent artificial neural network to provide a thrombus prediction from the memory filled, the second submission being immediately consecutive to the first submission; and resetting the memory.

9. The method according to claim 1, wherein the thrombus segmentation comprises a plurality of voxels identified as belonging to the thrombus, each voxel being associated with a false-positive label or a true-positive label, the false-positive label or the true-positive label being assigned by the secondary recurrent artificial neural network trained, the method comprising a step of refining the thrombus segmentation comprising the following sub-steps of:

calculating the lesion envelope from the lesion segmentation, distributing the thrombus segmentation into a first set of voxels and a second set of voxels:

the first set of voxels includes the voxels of the thrombus segmentation associated with the false-positive label, the second set of voxels includes the voxels of the lesion segmentation associated with the true-positive label, reducing the first set of voxels of the thrombus segmentation:

for each voxel of the first set of voxels, calculating the distance to the lesion, the distance to the lesion being the Euclidean distance from the voxel in the first set of voxels to the lesion envelope, ordering the voxels of the first set of voxels as a function of the distance to the lesion calculated, selecting a subset of voxels from the ordering of the voxels in the first set of voxels, selecting the segmentation corresponding to the merging of the second set of voxels and the subset of voxels selected as the thrombus segmentation.

10. The method according to claim 9, wherein the step of selecting a subset of voxels is performed by selecting the N voxels of the first set of voxels having the smallest distance to the lesion, N being between 3 and 5.

11. The method according to claim 9, wherein the step of selecting a subset of voxels is performed by selecting the voxels of the first set of voxels having a distance to the lesion less than a predetermined threshold.

12. The method according to claim 1, comprising a step of volumetrically characterising the thrombus from the thrombus segmentation.

13. The method according to claim 12, wherein the step of volumetrically characterising the thrombus comprises the following sub-steps of:

extracting the pixels of the thrombus segmentation from the thrombus segmentation, the pixels forming a point cloud contained in a volume, the volume being the maximum ellipsoidal envelope containing the thrombus, determining the geometric characteristics of the volume of the maximum ellipsoidal envelope containing the thrombus by principal component analysis of the point cloud along three main axes, the three main axes being orthogonal to each other, calculating the volume of the maximum ellipsoidal envelope containing the thrombus from the geometric parameters determined.

14. A non-transitory computer-readable recording medium comprising instructions which, when executed by a computer, cause the same to implement the steps of the method according to claim 1.

* * * * *